(12) United States Patent
Bouthillon et al.

(10) Patent No.: US 10,643,058 B2
(45) Date of Patent: May 5, 2020

(54) METHOD FOR EARLY DETECTION AND IDENTIFICATION OF MICROBIAL-COLONIES, APPARATUS FOR PERFORMING THE METHOD AND COMPUTER PROGRAM

(71) Applicants: MERCK PATENT GMBH, Darmstadt (DE); UNIVERSITE DE STRASBOURG, Strasbourg (FR); Centre National de la Recherche Scientifique (CNRS), Paris (FR)

(72) Inventors: Marine Bouthillon, Strasbourg (FR); Luc Felden, Andolsheim (FR); Ola Ahmad, Strasbourg (FR); Christophe Collet, Strasbourg (FR)

(73) Assignees: MERCK PATENT GMBH, Darmstadt (DE); UNIVERSITE DE STRASBOURG, Strasbourg (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 81 days.

(21) Appl. No.: 15/760,900

(22) PCT Filed: Aug. 17, 2016

(86) PCT No.: PCT/EP2016/001402
§ 371 (c)(1),
(2) Date: Mar. 16, 2018

(87) PCT Pub. No.: WO2017/045741
PCT Pub. Date: Mar. 23, 2017

(65) Prior Publication Data
US 2018/0349671 A1    Dec. 6, 2018

(30) Foreign Application Priority Data
Sep. 16, 2015  (EP) .................................... 15290231

(51) Int. Cl.
*H04N 7/18* (2006.01)
*G06K 9/00* (2006.01)
(Continued)

(52) U.S. Cl.
CPC ............. *G06K 9/0014* (2013.01); *C12Q 1/06* (2013.01); *G06K 9/00147* (2013.01); *G06K 9/40* (2013.01);
(Continued)

(58) Field of Classification Search
USPC ....... 382/100, 103, 106, 128–134, 162, 168, 382/172, 173, 181, 190, 199, 219, 224,
(Continued)

(56) References Cited

U.S. PATENT DOCUMENTS 5,694,478 A * 12/1997 Braier ...................... C12Q 1/04
382/133
6,418,238 B1 * 7/2002 Shiratani ............... G06T 7/0012
382/128
(Continued)

FOREIGN PATENT DOCUMENTS

EP    2372645 A2    10/2011
EP    2889366 A1    7/2015
(Continued)

OTHER PUBLICATIONS

International Search Report PCT/EP2016/001402 dated Nov. 28, 2016.

*Primary Examiner* — Seyed H Azarian
(74) *Attorney, Agent, or Firm* — Millen, White, Zelano & Branigan, P.C.; William Nixon

(57) ABSTRACT

The present invention is directed to a method for detection of microbial colonies on a surface, comprising the steps of obtaining one or a plurality of digital images I0, I1, I2, I3, I4 of the surface, said digital images I0, I1, I2, I3, I4 being
(Continued)

represented by at least two-dimensional matrices of pixel values, calculating a statistical noise distribution based on at least one of the digital images I0, applying the statistical noise distribution calculated in the calculation step to the one or the plurality of digital images I0, I1, I2, I3, I4, and detecting an object of interest as a candidate for a microbial colony based on deviation of pixel values from the noise distribution.

14 Claims, 5 Drawing Sheets

(51) Int. Cl.
    *C12Q 1/06*     (2006.01)
    *G06K 9/46*     (2006.01)
    *G06T 7/00*     (2017.01)
    *G06K 9/40*     (2006.01)

(52) U.S. Cl.
    CPC .............. *G06K 9/46* (2013.01); *G06T 7/0016* (2013.01); *G06T 2207/10028* (2013.01); *G06T 2207/20076* (2013.01); *G06T 2207/30024* (2013.01)

(58) Field of Classification Search
USPC ........ 382/232, 254, 260, 274–276, 286–291, 382/305, 312, 321; 348/80, 79
See application file for complete search history.

(56) References Cited

U.S. PATENT DOCUMENTS

| | | | |
|---|---|---|---|
| 6,718,068 B1* | 4/2004 | Gindele | G06T 5/002 |
| | | | 382/254 |
| 2006/0280352 A1 | 12/2006 | Muschler | |
| 2014/0293036 A1* | 10/2014 | Ddecaux | G01N 21/255 |
| | | | 348/80 |
| 2017/0044588 A1* | 2/2017 | Felden | G06K 9/00134 |
| 2018/0129864 A1* | 5/2018 | Robinson | G06T 7/0012 |

FOREIGN PATENT DOCUMENTS

| | | |
|---|---|---|
| GB | 2494202 A | 3/2013 |
| WO | 2001042786 A2 | 6/2001 |
| WO | 2001059157 A2 | 8/2001 |
| WO | 2003077552 A1 | 9/2003 |
| WO | 2014017480 A1 | 1/2014 |

\* cited by examiner

METHOD FOR EARLY DETECTION AND IDENTIFICATION OF MICROBIAL-COLONIES, APPARATUS FOR PERFORMING THE METHOD AND COMPUTER PROGRAM

The present invention relates to a method and a device for testing, respectively detecting, growing of microorganism on a surface. Especially, the present invention concerns an improved statistical processing of the image data of a surface, which is configured to exhibit growth of microorganism.

Many diseases can be borne and spread in human body through contaminated food or water, bad-quality pharmaceutical drugs, and other elements. For this reason, the quality of the industrial products becomes one of the crucial problems, specifically for the pharmaceutical and food-processing industries. Nowadays, tests of contamination take several days, up to 21 days, which becomes expensive and too long. Automatic techniques enabling an early detection of the contaminating microorganisms with high precision, and very small error rate (false positives) are of great help for achieving robust and optimized controls within relatively few days.

For example, in the pharmaceutical industry many processes are performed in a clean room environment. Examples of these processes include the filling of syringes and others. It is essential to monitor strictly the clean room condition in order to surely avoid a contamination of the final product. Therefore, it is usual to introduce into the clean room a carrier, a small dish, with a surface especially adapted for the growing of microorganism.

Many of the known methods for detecting the growth of microorganism on a surface are based on an optical inspection of the surface and on the identification of microbial-colonies based on a threshold level or a shape evaluation of microbial-colonies.

However, it presently takes a relatively long time to identify surely the growth of microorganism on a surface, i.e. it might take several days to obtain a reliable result. Trying to accelerate this process in the past has resulted in a large number of false positive results and have thus negatively affected the yield of the entire production process. This is due partly to noise included in the data obtained by imaging the surface. If the threshold level is too high, it takes a long time before the growing microorganism have reached the threshold level. On the other hand, if the threshold level is too low, many noise artifacts might lead to large number of false positive results.

Several technologies have been developed in the last decades that integrate optical systems with computer vision techniques for fast and automated detection, as well as counting and classification of microbial-colonies, and bacteria cells. The fluorescence imaging technique is one of them for detecting and enumerating the microbial-colonies. This technique shows efficiency and good recovery ratio (>90%) in optimal growth conditions of microorganisms, but it is not convenient for faster contamination tests.

As an alternative, image-based approaches have been used for both the detection and the discrimination of microbial-colonies using laser scatter-meter technique. A laser light illuminates an agar plate, which incubates the microbial-colonies, then, scatter patterns have been captured and recorded using a CCD camera to perform a 2D image with e.g. 256 gray levels. This technique uses a supervised training process applied on a large set of samples in order to identify the prototypes of the microbial-colonies using a combination of a large number of features such as Zernike and Chebyshev moments, or Haralick descriptors. This technique is highly time-consuming, and it is not well adapted for the detection and the identification of microbial-colonies during their first growth, and in low or weak concentrations, since there is no textural features or prior information that can be provided at that time for the detection and classification procedures.

Although, many image processing-based approaches have been established for the detection and identification of microbial-colonies, they are still traditional, and they do not fit with the most common and innovative optical techniques used nowadays (images are noisy and have low SNR (Signal-to-Noise-Ratio) in the framework of early detection), and with the severe industrial conditions that require short incubation periods, and the low concentrations of microorganisms (rare events) that might be present.

Furthermore, the reliability and the efficiency of most of these methods depend often on conditions that can be considered as limitations: colony morphology dependence (e.g. circular shape, internal distribution of proteins, molecular structure), colony distribution dependence (e.g. separated microbial-colonies), sample size, computation complexity, required prior information, which implies manual testing/processing.

On the other hand, there is a great need to design a method that can perform early detection with reliable results, highly robust to the noise formed by any imaging system, and independent of the morphology of the microbial-colonies. Then classification and counting can be well-established.

It is therefore an object of the invention to provide a device and a method for surely and quickly identifying the growth of microorganism on a surface.

The above object is achieved by means of the method of claim 1, by the apparatus of claim 10 and by the computer program of claim 16. The dependent claims are directed to different advantageous aspects of the invention.

The basic concept of the invention is to perform a statistical evaluation on the image data obtained from the surface so as to determine the model and the parameters of the noise distribution. Values of image parts/pixels not fitting into the expected noise distribution will be identified as possible microorganism.

In order to increase the reliability of the detection the processing might be repeated on image data of the same surface obtained at a later time point. This is a first approach that relies on time analysis of the data and that will allow to discriminate between false positive and real events based on the evaluated data.

As an alternative the same data of the image surface will be processed using different filters, e.g. smoothing filters. Smoothing the data allows to consider different scales for the detection and thus facilitates the detection of a colony having a large area compared to that of the image, multiple colonies covering a large area of the image or colonies with specific characteristics like molds.

Finally, in a third alternative both above approaches can be combined and the time and spatial characteristics of the microbial-colonies can be taken into account.

Especially, the present invention provides a method for detection of microbial-colonies on a surface, comprising obtaining one or a plurality of digital images of the surface, said digital images being represented by at least two-dimensional matrices of pixel values; calculating a statistical noise distribution based on at least one of the digital images, applying the statistical noise distribution calculated in the calculation step to the one or the plurality of digital images, and detecting an object of interest as a candidate for a microbial colony based on deviation of pixel values from the noise distribution.

It is preferred that the method, further comprises the step of obtaining the plurality of digital images by imaging the same surface at different times.

It is further preferred that the method comprises in the object detection step an identifying of those objects of interest as microbial-colonies, which show a time dependent growth based on two or more digital images.

According to a further embodiment the method comprises the steps of obtaining a first digital image by imaging a surface, and obtaining any further digital image of the plurality of digital images by applying a respective smoothing filter to the first digital image.

Additionally it is preferred that the method comprises the step of obtaining any further digital image of the plurality of digital images by applying a respective smoothing filter to the first digital images.

The invention further suggests that each image obtained by imaging the same surface at different times is used to obtain a plurality of images by applying the steps of a) determining one of the images obtained by imaging the same surface at different times as a first digital image, and b) obtaining any further digital image of the plurality of digital images by applying a respective smoothing filter to the first digital image, and c) repeating steps a) and b) for each image obtained by imaging the same surface at different times.

In the method of the invention the pixel values are values representing the relative height of a point or area of the surface.

Additionally, it might be considered to apply a mathematical correction function to the pixel values for compensating any curvature of the surface, before calculating the statistical noise distribution.

Particularly, the statistical noise distribution can be modelled as a Gaussian random field.

Although the invention has been described by method features, the invention is not limited to this method. The invention also includes a device especially configured to carry out any of the above methods.

Finally, the invention can be realized in form of a computer program comprising a computer program code, which when loaded into the internal memory of a computer will cause the computer to perform the method of the invention as described above.

In the following, preferred embodiments of the invention will be described with reference to the drawings, which show:

The present method is based on the background, on the contrary of the other methods in the prior art that are based on the microbial-colonies. They rely mainly on their shape, recognizing circular contour for example. There are several solutions to solve the detection problem and to identify the microbial-colonies as seen in the prior art. Nevertheless, these solutions do not provide a complete analysis and robust detection results against noisy data in our case, which means many pre-processing and/or post-processing and/or de-noising steps are required to detect and identify the microbial-colonies with little number of false positives.

Figure 1:
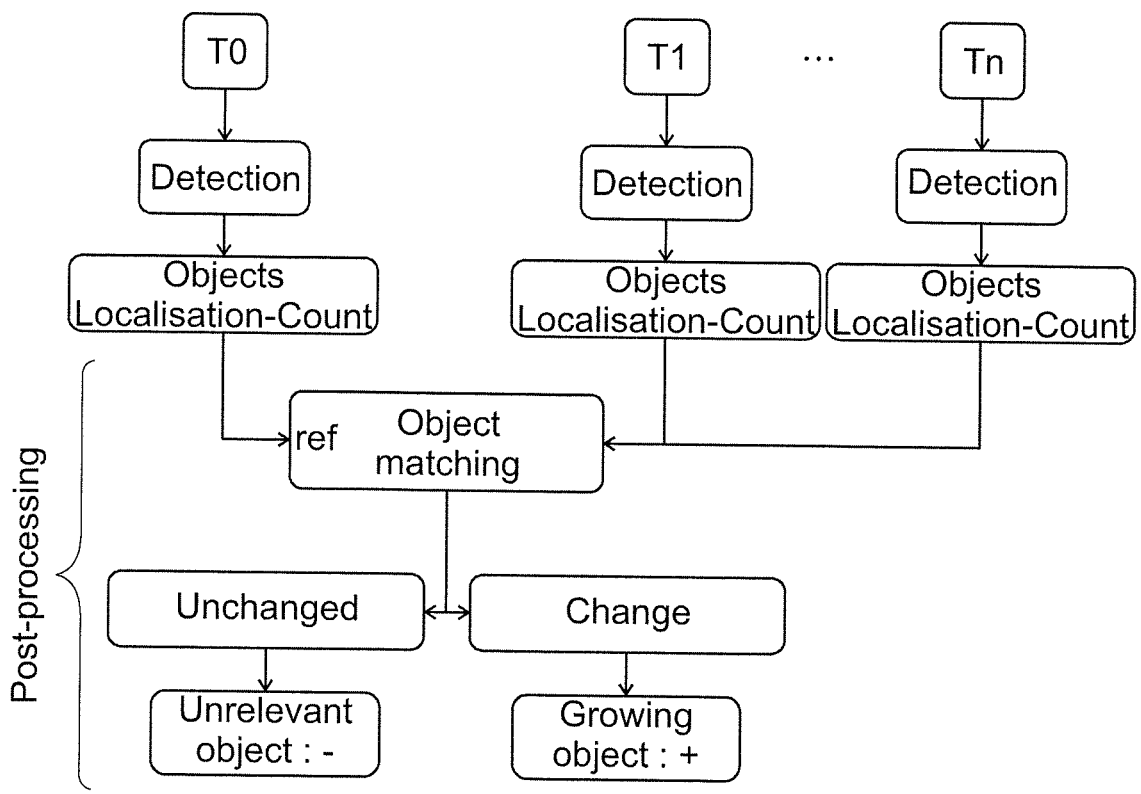
FIG. 1 a flow diagram of the first embodiment.

This first embodiment, as shown in FIG. 1 and as described above, is based on modeling the background image, and searching for the microbial-colonies in the background image, using the assumption that microbial-colonies are rare signals in the background image. The most common and used probabilistic models in modeling engineered surfaces are Gaussian and skew-Gaussian processes. Other models like beta, log-normal, gamma or Rayleigh distributions also exist, but they are less attractive. Gaussian processes are the most attractive models because they are simple models completely and uniquely determined by their first and second order moments, and they are computationally fast. However, a 'Gaussianization' (the fact to change the data so that they correspond to a Gaussian model) can be feasible and it often provides good solution for fitting data of non-Gaussian or unknown models. One can use a kind of orthonormal transformations like the PCA and ICA which give the most potentially 'Gaussianizable' components of the unknown PDF (probability density function).

In the case of the detection of contaminating microbial-colonies during their early growth, no prior information are available. This leads to the implementation of an unsupervised method. The microbial-colonies must be distinguished from the topographic surface roughness. The roughness topography can be represented by real 2D images modeled by a stationary Gaussian random field.

For the following discussion the definition of Gaussian random fields will be restricted to the case of two-dimensional images, where the space is represented on a sampled lattice by a collection of pixels.

Considering a pixel $x \in S$, where $S \in R^N$, (N=2 in our case), is the support space of the image, and let $Z(x)$ be the value of the relative height at the pixel x, then, $\{Z(x): x \in S\}$ defines a Gaussian Random Field (GRF), if for every choice $x_1, x_2, \ldots, x_n$, and any arbitrary n, the peak values $Z(x_1)$, $Z(x_2), \ldots, Z(x_n)$ follow a multivariate Gaussian distribution function with probability of the following form:

$$f_Z(z) = \frac{1}{(2\pi)^{\frac{n}{2}} |C|^{\frac{1}{2}}} e^{-\frac{1}{2}(z-\mu)C^{-1}(z-\mu)^t} \quad (1)$$

with mean vector $\mu = E|z|$, and n×n non-negative (or semi-positive) definite covariance matrix C, of the elements $C_{ij} = E[\{Z\{x_i\} - \mu_i)(Z(x_j) - \mu j)]$, and determinant $|C| = \det(C)$.

A Gaussian random field is stationary in both wide and strict sense if its mean $E|z|$ is constant (independent of locations in the image), and its covariance function $C_{ij} = C(x_i - x_j)$, for any integers (i,j), depends only on the difference $x_i - x_j$. If the covariance function depends only on the Euclidean length |.| of the difference between any two locations, such that $C_{ij} = C(|x_i - x_j|)$, then, the GRF is said isotropic or homogeneous. Generally, the mean can be subtracted from Gaussian random fields, so as to work with zero mean GRFs. In this case, an image that can be modeled by homogeneous zero-mean GRF will have a covariance function invariant under translations and rotations.

The validity of this model have been tested on the images of roughness topography in the absence of microbial-colonies.

The validation of the model (test of gaussianity) is performed by estimating the roughness parameters of the surface observations, and from the histogram data analysis as well as from fitting the geometric funtionals (e.g. Minkowski functionals and Euler characteristic function) of the surface to the Gaussian ones.

A statistical analysis based on this model is then applied in order to detect as early as possible the presence of the different types of microbial-colonies over the roughness topography. This analysis uses the notion of excursion sets, which will help to estimate a detection threshold. All pixels forming clusters with values higher than that threshold will be considered as objects of interest.

The detection threshold is estimated and used to get all the candidate clusters that may correspond to microbial-colonies. All the clusters given by one threshold value belong to an excursion set.

The notion of the excursion sets was defined for any measurable, real valued function defined on measurable subsets. The excursion set that will be obtained from the Gaussian random fields will be called Gaussian excursion sets.

The importance of the excursion sets comes from the need to adopt a geometric approach carried over these sets, and more specifically in the case where these sets are computed from random fields. Then, expectations about their geometric features could be derived. Such geometric approach helps estimating the detection threshold.

The geometry of the excursion sets of random fields was developed using both integral geometry and differential topology frameworks, and allows the definition of the notion of Euler Characteristic (EC), (denoted $\chi$ (Az(Z,S))), to describe the adjacency between points in the excursion sets and its topological features, or in other words the connected components.

For example, an excursion set might be composed of binary components and some of them may contain closed regions of background, called "holes". The EC, in this case, counts the number of connected components minus the number of holes.

For high level excursion sets, and suitably regular random fields, the EC counts the number of connected components, or clusters.

This concept of excursion sets and Gaussian random fields are well known to those skilled in the art of statistical data processing and will not be detailed here any further.

A statistical analysis based on the Gaussian random field is then performed to test the significance of the detected clusters and to control the probability of detecting false positives.

It consists in applying peak height and spatial extent tests to infer if the detected regions match, with high probability of presence, with microbial-colonies of interest, or if they belong to the noise (false alerts).

The first threshold is obtained from Euler-characteristic function, which approximates the mean number of local maxima. This test enables detecting all the potential colonies of sharp peak intensity values The second test is applied to the mean size of the objects detected by setting a threshold lower than a value which is obtained above. Applying this test on the background image only means that the probability of getting objects of relatively large size may occur by chance, contrary to the case of background image including microbial-colonies. This test enables detecting objects of low peak values and significant size.

Based on this theory the invention proposes the following method for using data obtained from an image of surface roughness profile at time tin order to obtain as a result those clusters indicating microbial-colonies.

fix an error rate ε to 0.01;
estimate z using a Gaussian random field approach and a corresponding excursion set for 5% test of significance;
detect all the candidate clusters at z and z−0.7;
for all candidate clusters do
calculate P(h>h0));
calculate P(sz>s0);
accept clusters that satisfy P(h>ho)<ε or P(sz>s0)<ε
Where z: threshold level
ho: maximum height above z
h: height of one cluster detected above z
so: size threshold
sz: size of one cluster detected above z
ε: error rate $$P(h \geq h_0) = \frac{E[m_{z+h_0}]}{E[m_z]} = (1 + h_0/z)e^{-(zh_0+h_0^2/2)}$$

$$E[s_z] = \lambda(S)\Phi(-z)/E[m_z]$$

Where φ is the normal cumulative distribution function. The term $\lambda(S)\phi(-z)$ is the mean area of the excursion set $\lambda z(Z,S)$ of the Gaussian random field above z. Then, the marginal probability for spatial extent of one cluster of size sz≥s0 above a threshold z can be expressed as $$P(s_z \geq s_0) \approx E[s_z] = e^{-\beta s_0}$$

In the following some examples illustrating the invention will be discussed.

Two different types of micro-porous membrane filters were used with different standard agar plates (R2A, TSA (Triptic Soy Agar), SDA (Sabouraud Dextrose Agar)). One of the membranes is composed of mixed cellulose ester, hydrophilic 47 mm and 0.45/μm pore size, white gridded (HAWG04700 [15]), and the second is Durapore membrane, PVDF, hydrophilic, 47 mm and 0.45 μm pore size, white, gridded. These membranes will be referenced as HA and HV, receptively. The bacterial culture strains used in the contamination tests are the following: *Pseudomonas aeruginosa* ATCC 9027, *Methylobacterium mesophilicum* ATCC 29983, *Dekkera anomala* CBS 77 and *Aspergillus brasiliensis* ATCC 16404. The samples were filtered through the membranes HA and HV, and the membranes are placed onto the agar plates and incubated within environmental conditions recommended for the growth of the microbial-colonies. Several incubation periods were considered to assess sufficient samples for both tests and validation.

The total number of samples used are 40 ones obtained from both membranes including the four species of bacterial strains.

The membranes, before incubation and after each incubation period, were placed along the optical axis of a measurement device.

The optical measurement system is composed of a laser diode light of 405 nm wavelength, and a digital camera inclined with respect to the laser line. The laser beam is emitted to illuminate a line profile (800 points through the X-axis) of one membrane placed perpendicular to the light axis (X-axis). The displacement through the Y-axis enabled scanning 15768 profiles, and the reflected light from each point of the profiles is recorded by the camera forming 2D images (800×15768 pixels) of the membrane's roughness topography. All the optical components are installed on a breadboard to enable stable positioning and less vibration effects.

Due to the inclination of the camera, the profiles measured from the membranes will be sloped either or not linearly, depending on the form of the membranes, generating in this case a curved surface and undesired gross geometry which should be corrected. The membrane samples are nominally flat, however, in reality there is still some tilt over the sample length which yields a curved surface generation from acquisition. So, a second order polynomial fit is used to remove such errors using the least squares algorithm, and then subtracting the fitted curved surface from the profile data. A 3×3 median filter is then applied to remove the outliers and to increase the signal to noise ratio without losing the desired information located at high frequencies. The images are then normalized by subtracting the mean and dividing each pixel by the standard deviation to obtain values of zero mean and unit variance.

In the following, each image will include two classes of data: roughness topography (noise), and microbial-colonies. The method is applied to the images acquired from the contaminated membranes at incubation periods t0, t1, t2, t3, and t4, where t0 represents the first day before incubation (microbial cells remain under resolution at this time), t1 is the first day of the bacterial growth, and t4 represents the last day of the incubation period. The microbial-colonies starts to grow at time t2, and some of them become to be recognized obviously by the measurement system at time t4 or before. The method is applied through the incubation periods to demonstrate its ability to achieve a very early detection when the microbial-colonies can hardly be recognized. In the case of images with no microbial-colonies, the experimental global maximum value of the profile was obtained at 4.59, while the approximate maximum obtained analytically using Euler characteristic for the p-value <0.05 was $z=5.07$, and $z=5.4$ for p-value <0.01.

When the images include microbial-colonies, the peak values of the microbial-colonies are relatively higher than z for both 5% and 1% significance, which insures detecting very few number of false positives above z.

The microbial-colonies were robustly detected with precision 100% for thresholds computed at 0.05 test of significance and more than 95% for 0.01 test of significance, during the periods t0 and t4. The number of false positives due to the detection error is less than 1%.

In summary, the main objective of the invention is to introduce a robust and automated method that enables early detection of microbiological contaminations from biological surfaces (membranes) measured by a topographical imaging device. The measurements are represented by 2D images including both the roughness topography (noise) and the microbial-colonies. A statistical analysis was derived from the theoretical framework of Gaussian random fields, in order to estimate the detection threshold that separates the microbial-colonies from noise.

The method presents very good results, and less sensitivity to false positives over all incubation periods.

As discussed above regarding an embodiment of the invention, the method for detecting microbial-colonies is based on the use of a model of the background image. The model allows the calculation of parameters (based on the data) that will allow the detection. Those parameters can also be used to characterize what is detected.

The embodiment allows to obtain "Objects", i.e. possible microbial-colonies form, to localize the objects and to count them.

In the case of adding non-living germs to the membranes, then another type of false positives should be removed, otherwise, the method will indicate a presence of microbial-colonies even in the case of no microbial-colonies.

It could be shown that implying a matching procedure between the detected clusters before and after incubation periods may help removing the objects that do not belong to microbial contamination.

After the step localization and counting of the object of an image, an "Object matching" step between the data of images obtained at different times might be implemented, as shown in FIG. 1. In this way a verification of possible microbial-colonies is achieved by the shown post-processing.

In case of changes in a matching object the respective object is marked as a "Growing Object", otherwise it is marked as irrelevant.

That is, if the reference image includes insignificant particles/objects, the above post-processing is performed in order to identify the microbial-colonies from these particles by comparing reference acquisition with the others.

Generally, the method showed robust and good results. Nevertheless, the matching criterion is empirical and it depends on the image resolution, and it is sensitive to any possible misregistration between the reference and current images, so if the detection threshold does not lead to obtain the entire object, or the misregistration is of order of multiple pixels false microbial-colonies would be detected.

Figure 2:
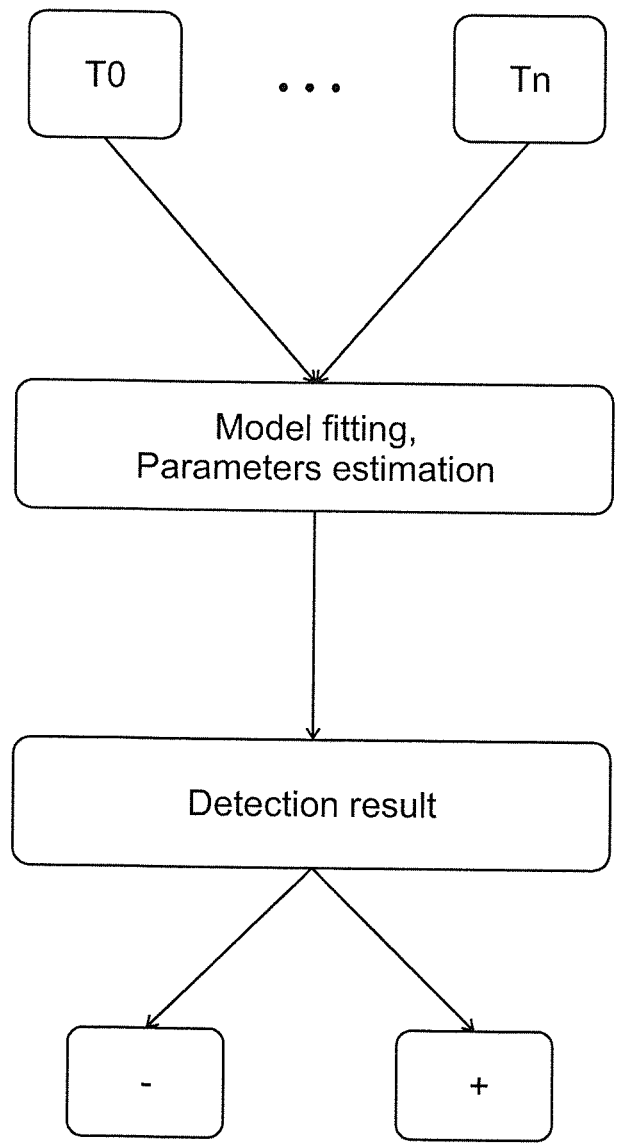
FIG. 2 a flow diagram of the second embodiment.

As a consequence, the present invention proposed a second embodiment, as shown in FIG. 2 that modifies the first embodiment without the use of a post-processing stage.

This second embodiment include the time in the model (space-time analysis).

To differentiate between microbial-colonies and other similar objects without the use of a post-processing stage, time is added to the detection process. At least two acquisitions are made, with the first at t0 and the others during growth.

Microbial-colonies are not isolated on the surface medium; there are some particles that may also be present on that surface which are not significant. So, in order to avoid applying a threshold to each acquired image and then process the detection results from each threshold, the idea of the second embodiment of the present invention is to construct one model (i.e., one detection threshold) that deals with time series images obtained through different incubation times.

The first image is the background image and the following (n-I) ones are images including microbial-colonies during their time growth.

This embodiment showed better results than the first one in the sense of microbial-colonies identification.

Nevertheless, this model is applied to images with respect to the resolution of the acquisition, which may have a non-negligible impact on the robustness of the detection (estimated threshold).

Furthermore, there might be a need to characterize the detected microbial-colonies, like for example estimate their size and geometric features.

Figure 3:
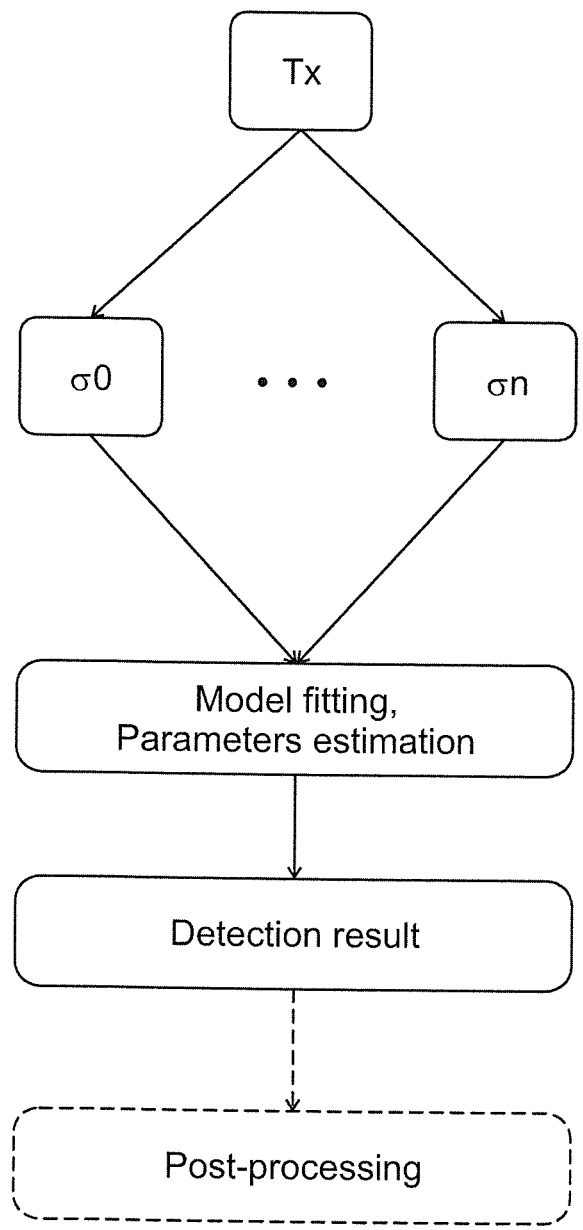
FIG. 3 a flow diagram of the third embodiment.

Generally, the microbial-colonies observed by any optical device will behave differently according to the scale of observation and leading to multiple levels of noise observations. To deal with these issues, the invention proposes a third embodiment, as shown in FIG. 3.

The third embodiment includes a scale-space analysis to both detect objects of any size and estimate their true size. The noise is always present, coming from the background, the acquisition system, etc. It is quantified by the Signal to Noise Ratio (SNR), and in the case of low SNR (the objects are similar to the noise), they are hard to detect. An improvement is then to consider the signal at several scales. It means that the image is smoothed at several degrees. This smoothing enables getting better SNR, and better matching of the object signal. The embodiment suggests to integrate a scale-space strategy to the detection process by an appropriate model, for both better detection and parameters computation or characteristics.

A solution based on scale-space modeling is used to decompose the image into several scales thus to obtain multiple images, each one corresponding to a specific scale.

For best detection results, the smoothing filter is chosen to fit the general shapes of the microbial-colonies. The second and third embodiments are both complementary solution and required in the application of this invention.

The second embodiment addresses the problem of object identification and discrimination, and the third embodiment is designated to improve the SNR for better detection and object characterization. Nevertheless, applying each solution independently depends on the application needs. For the application of this invention, using one embodiment is not computationally exhaustive, and applying more than one successive embodiment may transform non desirable results from one solution to the other (bias of the result of one solution affected by an error of the second one). Thus, a fusion procedure that merges both second and third embodiment is proposed as a complete and robust solution.

Figure 4:
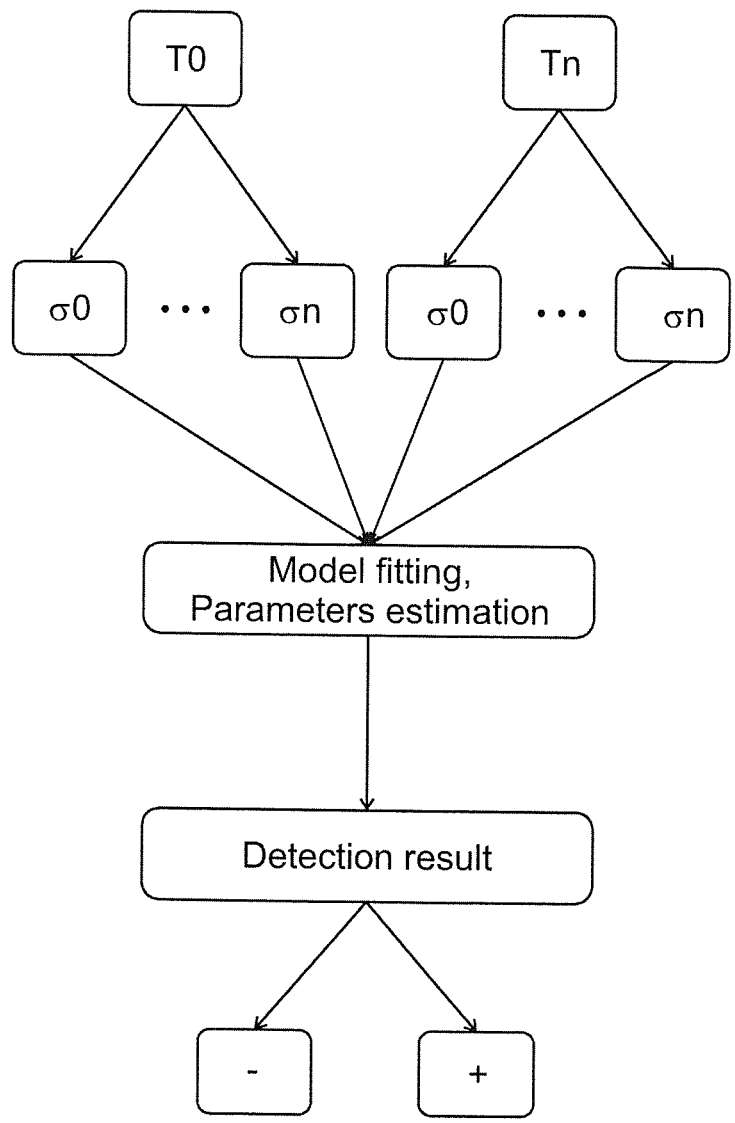
FIG. 4 a flow diagram of the fourth embodiment.

The idea of this fourth embodiment, as shown in FIG. 4, is to construct a complete and unified model that merges both scale and time criteria given by second and third embodiments. A spatio-temporal scale-space model is constructed to model the (n) time series images in the case of the absence of microbial-colonies (the null hypothesis case). So that, when the model is applied to the null hypothesis, each detection is considered as a false positive, and hence, the number of false positives can be bounded. Otherwise, when the model is applied to the data including microbial-colonies each detection will be considered true, as the case of all the previous embodiments, with one difference related to get best minimized number of false positives and less biased results. Here, the model integrates both scale-space and space-time embodiments.

At least two images are acquired at different incubation times and each one is smoothed by scale-space filters.

According to the present invention, once detected with the described method of any of embodiments one to four, the microbial-colonies can be counted. Such solution can then be integrated to application for bio-burden study, with a robust count.

Indeed, the system will not take into account the objects that are not microbial-colonies, and will be able to differentiate and count clusters of microbial-colonies thanks to the improved contour and shape delimitation. Additionally, when using space-time and/or scale-space, characteristics of the microbial-colonies can be obtained, which can be used for identification of for example a growth rate, a size, geometric features (contour, elongation, diameter, . . . ), a scale, a lifetime of the microbial-colonies over the scale interval and so on.

Embodiment three including scale-space is well adapted to the study of the geometric features of the microbial-colonies because it allows a very robust localization and delimitation of microbial-colonies. It provides better estimation of the area, contour and so on. The extracted features can be considered as prior information to be analyzed in traditional machine learning methods.

The method can robustly detect microbial-colonies at early stage of growth.

The invention provides a fast and computationally efficient method. It aims at bounding and minimizing the number of false positives, so it is robust and provides lower false detections than other methods in the prior art.

The smoothing filters of the third or fourth embodiment can be adapted to fit any shape of microbial-colonies using a bank of filters of varying characteristics.

The invention can achieve both detection and discrimination simultaneously at one time without post-processing.

The invention, as defined in the first and third embodiment can be applied to one image including isolated microbial-colonies without using the time growth criteria.

The method provides scale, size, and other geometrical features, time growth interval and microbial-colonies lifetime over the scale interval that can be used for characterizing micro-colonies for classification purposes.

In the case of the use of the fourth embodiment that integrates time and multi scale-analysis, the invention proposes the use of a spatio-temporal scale-space Gaussian random field. The microbial-colonies are often not isolated and insignificant particles can be present with microbial-colonies on the membrane surface. In this mode of operation, the growth criterion of the microbial-colonies is used and the time interval satisfies (tn−1−t0>0).

Figure 5:
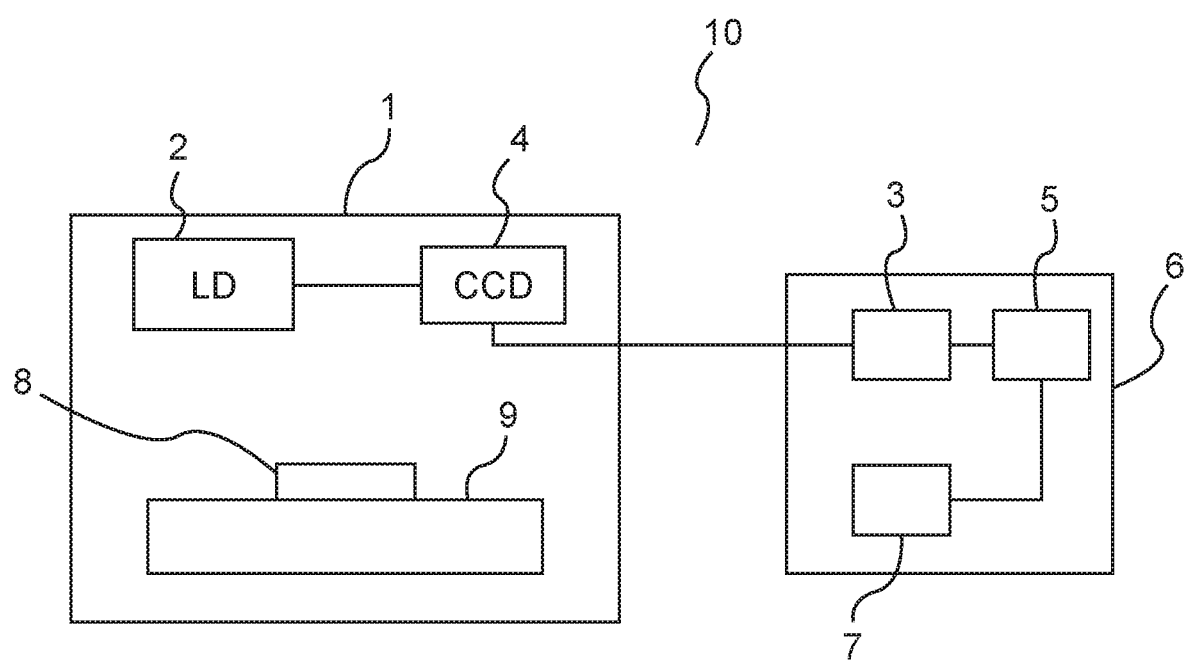
FIG. 5 an apparatus for performing the invention.

Although, the invention has been described based on a method, the invention of course can be implemented as an apparatus 10 comprising a device 1 for obtaining one or a plurality of digital images of the surface 8, said digital images being represented by at least two-dimensional matrices of pixel values, a computer 6 having a processor 3 for calculating a statistical noise distribution based on at least one of the digital images, a processor 5 for applying the statistical noise distribution calculated in the calculation step to the plurality of digital images, and a detector 7 for detecting an object of interest as a candidate for a microbial colony based on deviation of pixel values from the noise distribution, as shown in FIG. 5.

Device 1 for obtaining one or a plurality of digital images of the surface can be a charge-coupled device (CCD) camera 4 to perform a 2D image with 256 gray levels and can include a laser diode (LD) 2, as described above. They can further include a stage 9 or desk for holding the samples on the surface 8 relative to the camera 4 and the laser diode 2.

Processor 3 for calculating the statistical noise distribution, processor 5 for applying the statistical noise distribution, and detector 7 for detecting an object of interest can be implemented as a computer 6.

Although the invention has been described with regard to embodiments one to four, the invention is not limited to these embodiments. As discussed, different approaches, other than Gaussian random fields, might be used.

The invention claimed is:

1. Method for detection of microbial colonies on a surface within an apparatus, comprising:
obtaining one or a plurality of digital images (I0, I1, I2, I3, I4) of the surface using a charge-coupled device (CCD) camera and a laser diode, said digital images (I0, I1, I2, I3, I4) being represented by at least two-dimensional matrices of pixel values;
applying a mathematical correction function to the pixel values for compensating any curvature of the surface;
calculating a statistical noise distribution based on at least one of the digital images (I0) received from the CCD camera;

applying the statistical noise distribution calculated in the calculation step to the one or the plurality of digital images (I0, I1, I2, I3, I4); and detecting an object of interest as a candidate for a microbial colony on the surface based on deviation of pixel values from the noise distribution, wherein the pixel values captured by the CCD camera are values representing the relative height of a point or area of the surface.

2. The method of claim 1, further comprising the step:
obtaining the plurality of digital images (I0, I1, I2, I3, I4) by imaging the same surface at different times (T0, T1, T2, T3, T4) using the CCD camera.

3. The method of claim 2 where each image (I0, I1, I2, I3, I4) obtained by imaging the same surface at different times (T0, T1, T2, T3, T4) is used to obtain a plurality of images ((I0a, I0b, I0c, . . . ), (I1a, I1b, I1c, . . . ), (I2a, I2b, I2c, . . . ), . . . ) by applying the steps of:
a) determining one of the images (I0, I1, I2, I3, I4) obtained by imaging the same surface at different times (T0, T1, T2, T3, T4) as a first digital image (Ii); and
b) obtaining any further digital image of the plurality of digital images (Iia, Iib, . . . ) by applying a respective smoothing filter to the first digital image (Ii);
c) repeating steps a) and b) for each image (I0, I1, I2, I3, I4) obtained by imaging the same surface at different times (T0, T1, T2, T3, T4).

4. The method of claim 1, wherein the object detecting process comprises:
identifying those objects of interest as microbial colonies, which show a time dependent growth based on two or more digital images (I0, I1, I2, I3, I4).

5. The method of claim 1, further comprising the step:
obtaining a first digital image (I0) by imaging the surface using the CCD camera; and
obtaining any further digital image of the plurality of digital images (I0, I1, I2, I3, I4) by applying a respective smoothing filter to the first digital image (I0).

6. The method of claim 1, further comprising the step:
obtaining any further digital image of the plurality of digital images ((I0a, I0b, I0c, . . . ), (I1a, I1b, I1c, . . . ), (I2a, I2b, I2c, . . . ), . . . ) by applying a respective smoothing filter to the first digital images (I0, I1, I2, I3, I4).

7. The method of claim 1, wherein the statistical noise distribution is modelled as a Gaussian random field.

8. A non-transitory computer-readable medium having a computer program code encoded thereon, which when the computer program code is loaded into the internal memory of a computer will cause the computer to perform the method of claim 1.

9. An apparatus for detection of microbial colonies on a surface, comprising:

a device (1) for obtaining one or a plurality of digital images (I0, I1, I2, I3, I4) of the surface using a charge-coupled device (CCD) camera and a laser diode, said digital images (I0, I1, I2, I3, I4) being represented by at least two-dimensional matrices of pixel values;

a first processor configured to apply a mathematical correction function to the pixel values for compensating any curvature of the surface;

the first processor (3) configured to calculate a statistical noise distribution based on at least one of the digital images (I0) captured by the CCD camera;

a second processor (5) configured to apply the statistical noise distribution calculated in the calculation step to the plurality of digital images (I0, I1, I2, I3, I4); and a detector (7) to detect an object of interest as a candidate for a microbial colony on the surface based on deviation of pixel values from the noise distribution, wherein the pixel values captured by the CCD camera are values representing the relative height of a point or area of the surface.

10. The apparatus of claim 9, wherein the device for obtaining the plurality of digital images (I0, I1, I2, I3, I4) is configured to image the same surface at different times (T0, T1, T2, T3, T4) using the CCD camera.

11. The apparatus of claim 10, wherein the device for obtaining the plurality of digital images (I0, I1, I2, I3, I4) is configured to obtain a first digital image (I0) by imaging the surface using the CCD camera, and to obtain any further digital image of the plurality of digital images (I0, I1, I2, I3, I4) by applying a respective smoothing filter to the first digital image (I0).

12. The apparatus of claim 10, wherein the device for obtaining the plurality of digital images (I0, I1, I2, I3, I4) is configured to obtain the pixel values as the values representing the relative height of a point or area of the surface.

13. The apparatus of claim 10, wherein
the device obtains any further digital image of the plurality of digital images ((I0a, I0b, I0c, . . . ), (I1a, I1b, I1c, . . . ), (I2a, I2b, I2c, . . . ), . . . ) by applying a respective smoothing filter to the first digital images (I0, I1, I2, I3, I4).

14. The apparatus of claim 10, wherein the apparatus is configured to:
a) determine one of the images (I0, I1, I2, I3, I4) obtained by imaging the same surface at different times (T0, T1, T2, T3, T4) as a first digital image (I0); and
b) obtain any further digital image of the plurality of digital images (I0, I1, I2, I3, I4) by applying a respective smoothing filter to the first digital image (I0);
c) repeat steps a) and b) each image (I0, I1, I2, I3, I4) obtained by imaging the same surface at different times (T0, T1, T2, T3, T4).

* * * * *